United States Patent [19]
Hofmeister et al.

[11] Patent Number: 4,725,426
[45] Date of Patent: Feb. 16, 1988

[54] ESTROGENIC 17α-HALOGEN-VINYLESTRANES

[75] Inventors: Helmut Hofmeister; Henry Laurent; Paul E. Schulze; Rudolf Wiechert; Walter Elger, all of Berlin; Kunhard Pollow; Hans J. Grill, both of Mainz-Hechtsheim, all of Fed. Rep. of Germany

[73] Assignee: Schering Aktiengesellschaft, Berlin and Bergkamen, Fed. Rep. of Germany

[21] Appl. No.: 758,982

[22] Filed: Jul. 25, 1985

[30] Foreign Application Priority Data

Jul. 25, 1984 [DE] Fed. Rep. of Germany ....... 3427795

[51] Int. Cl.$^4$ .................. A61K 43/00; A61K 49/00; A61K 31/56; C07J 1/00
[52] U.S. Cl. ........................................ 424/1.1; 424/9; 260/397.5; 514/182
[58] Field of Search ............... 424/1.1, 9; 260/397.5; 514/182

[56] References Cited

U.S. PATENT DOCUMENTS 4,450,149 5/1984 Kabalka .
4,541,957 9/1985 Nakatsuka et al. .............. 260/397.2

FOREIGN PATENT DOCUMENTS 0137434 9/1984 European Pat. Off. .

OTHER PUBLICATIONS

The Journal of Nuclear Medicine, 23:5, May 1982, pp. 431–436, Hanson et al.
Jagoda et al, Journal of Nuclear Medicine, 25:4, Apr. 1984, pp. 472–477.
Chem. Abstracts, 100:7, 13, Feb. 1984, p. 536, Kabalka et al.
Chem. Abstracts, 86–95, 1977–1981, 10th Collect. Ed., 95:7, 17, Aug. 1981, p. 649, 61355c, Kabalka et al.

Primary Examiner—Leonard Schenkman
Assistant Examiner—Joseph A. Lipovsky
Attorney, Agent, or Firm—Millen & White

[57] ABSTRACT

17α-bromo-α and 17α-iodo-vinyl-estrane derivatives of general formula I

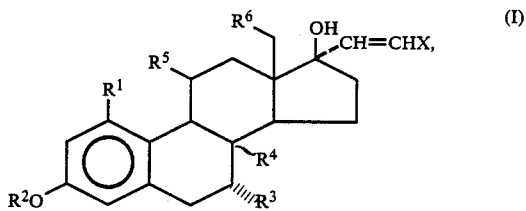

wherein
X is a bromine or iodine atom in Z or E position,
$R^1$ is hydrogen, hydroxy or acyloxy with up to 3 C atoms,
$R^2$ is hydrogen, alkyl with up to 3 C atoms and alkanoyl and aroyl with up to 7 C atoms,
$R^3$ is hydrogen or methyl,
$R^4$ is a hydrogen atom in the α or β position,
$R^5$ is hydrogen, methyl or methoxy and
$R^6$ is hydrogen or methyl, are pharmacologically effective with a profile of action like ethinylestradiol and in the form of their radioactively labeled compounds are also valuable diagnostic media.

The Z-isomers can be prepared by a new process by reaction of the corresponding 17α-ethinyl steroids with trialkyl (or phenyl) tin hydride with addition of a free radical former.

14 Claims, No Drawings

ESTROGENIC 17α-HALOGEN-VINYLESTRANES

BACKGROUND OF THE INVENTION

This invention relates to new 17α-halovinylestranes and their pharmaceutical use.

17α-(E-2-iodovinyl)-1,3,5(10)-estratriene-3,17β-diol in the E-configured estrogen series is known from the works of Hanson et al. (J. Nucl. Med. 23 (1982) 431). Also, the corresponding 3-methyl ether (Kabalka et al., Syn. Commun. 11 (1981) 247), the corresponding radioiodine compound (Kabalka et al., J. Label Comp. Radiopharm. 19 (1982) 795) and the 11β-methoxy compound, i.e., 17α-(E-2-iodovinyl-11β-methoxy-1,3,5(10)-estratriene-3,17β-diol (Jagoda et al., J. Nucl. Med. 25 (1984) 472) have already been produced. 17α-(Z-2-bromovinyl)-methoxy-1,3,5(10)-estratrien-17β-ol is known in the Z-configured estrogen series (Kabalka et al., Syn. Commun. 13 (1983) 1027).

Synthesis of these halogen vinyl steroids and also of radioiodovinyl compounds proceeds by 17α-(E-2-tributylstannylvinyl) derivatives or by the 17α-(E-2-vinylborane) compound. These are reacted with iodine or [$^{125}$I]iodine. The 17α-tributylstannyls are produced from ethinylestradiol or its 3-methyl ether, e.g., by reaction with tributyltin hydride with addition of a radical former, e.g., α-α'-azoisobutyronitrile in tetrahydrofuran, while E-17α-vinylborane is formed by hydroboration with organoboranes, e.g., catecholborane.

SUMMARY OF THE INVENTION

It is an object of this invention to provide new compounds having valuable pharmaceutical properties.

Upon further study of the specification and appended claims, further objects and advantages of this invention will become apparent to those skilled in the art.

These objects have been achieved by providing 17α-bromo-and 17α-iodo-vinylestrane derivatives of formula I

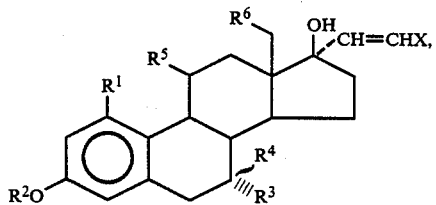

wherein
X represents a bromine or iodine atom in Z or E position,
$R^1$ is hydrogen, hydroxy or acyloxy of up to 3 C atoms,
$R^2$ is hydrogen, alkyl of up to 3 C atoms or alkanoyl or aroyl of up to 7 C atoms,
$R^3$ is hydrogen or methyl,
$R^4$ is a hydrogen atom in the α or β position,
$R^5$ is hydrogen, methyl or methoxy and
$R^6$ is hydrogen or methyl,
wherein the substituent X can also be a radiobromine or radioiodine isotope,
provided that $R^5$ is not methoxy when $R^1$, $R^2$, $R^3$ and $R^6$ are hydrogen, and X is iodine in E position; provided that $R^2$ is not hydrogen or methyl, when $R^1$, $R^3$, $R^5$ and $R^6$ are hydrogen, and X is iodine or radioiodine in E position; and provided $R^2$ is not methyl when $R^1$, $R^3$, $R^5$ and $R^6$ are hydrogen and X is bromine in Z position.

DETAILED DISCUSSION

The compounds of formula I are pharmacologically effective substances with a profile of action like the corresponding 17α-ethinyl compounds, e.g., the known estrogen ethinylestradiol. In the form of their radioactively labeled derivatives the compounds of formula I are also valuable components in diagnostic media.

The acyl portions in compounds of formula I can be derived from lower aliphatic (alkanoyl) or aromatic (aroyl) carboxylic acids such as, e.g., acetic acid, propionic acid or benzoic acid. Alkyl of up to 3 C atoms includes all lower alkyl radicals, e.g., methyl, ethyl, propyl and i-propyl. Alkanoyl includes formyl, acetyl, propionyl, butynyl groups, pentanoyl groups, hexanoyl groups and heptanoyl groups.

The compounds of formula I with an E configuration in the 17α side chain can be produced by methods known in the art, e.g., wherein a 17α-ethinylestrane derivative of the formula II

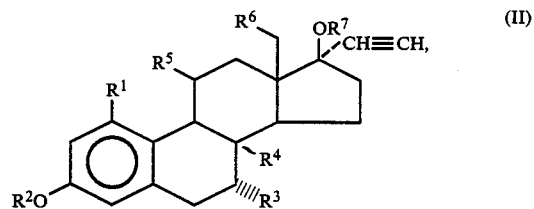

wherein
$R^{1-6}$ have the meanings given above and
$R^7$ is hydrogen, alkanoyl or arylcarbonyl of up to 7 C atoms, is reacted with a triphenyltin or trialkyltin hydride, of 2 to 6 C atoms per alkyl radical form to the corresponding 17α-(trialkyl(or phenyl)stannylvinyl) -estrane intermediate and then the trialkyl(or phenyl) stannyl radical is exchanged for bromine or iodine and, optionally, a free hydroxy group on the A ring is partially esterified or an acyl group in the 3 and/or 17α-position is saponified.

The reaction of compounds of formula II with triphenyltin hydride or a trialkyltin hydride with 2 to 6 carbon atoms per alkyl radical is performed in an inert solvent. Suitable solvents include for example, ethers such as diethyl ether, dioxane, tetrahydrofuran or 1,2-dimethoxyethane. The reaction is typically performed in the presence of a free radical former, e.g., α-α'-azoisobutyronitrile as catalyst. The subsequent exchange of the trialkyl(or phenyl)stannyl group for a bromine or iodine atom is performed in an inert solvent in the presence of agents yielding bromine or iodine cations. A suitable method, for example, is the reaction of organotin compounds in an inert solvent as, e.g., an ether such as dioxane, tetrahydrofuran or 1,2-dimethoxyethane with N-bromosuccinimide or N-iodosuccinimide. Other suitable methods are, for example, the processes described in the publications J. Nucl. Med. 23, 1982, 431, Appl. Nucl. Radiochem. 1982, 197 or Helv. Chim. Acta, 1982, 1018.

The compounds of formula I with a Z configured halo atom in the 17α side chain are preferably produced by a new process wherein a compound of formula II in a polar or non-polar solvent is treated with a triphenyltin or trialkyltin hydride of 2-6 C atoms per alkyl radical at temperatures of 20°–100° C. and then the 17α-(trialkyl-(or phenyl) stannylvinyl)-estrane so obtained is reacted with a compound yielding the necessary halogen.

For this purpose, the initial material of formula II, in an inert polar or non-polar solvent, e.g., tetrahydrofuran, 2-dimethoxyethane, acetonitrile, hexamethylphosphoric triamide, dioxane, isopropanol or N-methylpyrrolidone, is treated with trialkyltin or triphenyltin hydride at temperatures of 20°–100° C. No free radical former is added as catalyst as is done for the series of E-configured compounds. Depending on the reaction conditions, the reaction time lasts a few hours up to several days and at the longest is generally ended in four days. The triphenyltin or trialkyltin hydride is used in excess. The amount used is 2-to 10-fold relative to the amount of steroid. The course of this reaction was quite suprising. There was no way to predict that merely omitting the radical former in the reaction known in the art for producing E-configured compounds would lead to compounds that are Z-configured.

An alkanoyl group in the 3-position is saponified during the process. When a 3,17α-diacyloxy-1,3,5(10)-estratriene is used, the monoacylate is obtained, for example, in the 17 position. The subsequent exchange of the trialkyl(or phenyl) stannyl group for bromine or iodine occurs stereospecifically as in the E-configured series.

Aroyl groups optionally present in the 3-position or acyl groups optionally present in the 17-position can be split off with alkali by methods known in the art.

The compounds of formula II are all known or readily prepared using conventional reactions and known or readily prepared starting materials. See, e.g., U.S. Pat. No. 3,418,415, which is incorporated by reference herein.

The 17α(2-bromovinyl) steroids of formula I can be used as initial products for the production of the corresponding 17α-(2-radioiodovinyl) compounds. Thus, for example, the corresponding 17α-(2-[*I]iodovinyl compounds can be produced from 17α-(2-bromovinyl) steroids by exchange reaction with radioactive sodium [*I]iodide. Another method for production of 17α-(Z-2-[*I]iodovinyl) or 17α-(Z-2-[*Br]bromovinyl) steroids proceeds by means of 17α-(Z-2-tributylstannylvinyl) compounds which are reacted with Na ($^{125}$I) iodide of Na ($^{77}$Br) bromide.

Suitable radioactive iodine isotopes include, for example, the $^{124}$I, $^{125}$I, $^{126}$I or $^{131}$I isotope. Suitable radioactive bromine isotopes include, for example, the $^{77}$Br and $^{82}$Br isotope.

Both the Z and E configured 17α-bromo- and 17α-iodovinylestradiols of general formula I have a strong estrogen action. Particularly, the Z-configured 17α-halovinylestradiols show a substantially stronger binding on the estrogen receptor than do the isomeric E-17α-halogen vinylestradiols. Thus, the affinity for the estrogen receptor is three times stronger in 17α-(Z-2-iodovinyl)-1,3,5(10)-estratriene-3, 17β-diol than in ethinylestradiol, while the isomeric E-2-iodovinyl compound exhibits a considerably weaker receptor binding in comparison with ethinylestradiol (0.6x ethinylestradiol) but nevertheless is useful.

The compounds of formula I can, thus, be used for the purposes for which ethinylestradiol is known analogously to the latter. Typical unit dosages are 0.01–0.5 mg. Typical daily dosages, e.g., for humans, are in the range of 0.01–10 mg. Typical indications, uses (e.g., contraception, gynecological disorders) and regimens are well known. See, e.g., U.S. Ser. No. 552,537 of Nov. 16, 1983, now allowed, and U.S. Ser. No. 603,855 of Apr. 25, 1984, which entire disclosures are incorporated by reference herein.

The compounds of formula I with radioactive halogen are suitable as radio diagnostic media because of their strong receptor binding. Using scintiscanning, they can therefore be used for visualization of organs and tumors which contain estrogen receptors after they become occupied by the vinylhalogen steroids. In the case of women, the organs involved are especially the uterus and mammary glands. Further, the radiohalogenvinyl steroids can be used for detection of tumors and matastases in the tissues of these organs. Of particular interest are the 17α[$^{125}$I]-iodovinyl compounds, since they are suitable for in-vitro diagnostic media. In these radio-uses, the compounds can be used analogously as described in, e.g., the references cited above and incorporated by reference.

Of course, the compounds can also be conventionally used to prepare each other by conventional reactions.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

17α-(Z-2-iodovinyl)-1,3,5(10)-estratriene-3,17β-diol (a) 10.0 g of 3-benzoyloxy-17α-ethinyl-1,3,5(10)-estratrien-17β-ol in 200 ml of tetrahydrofuran is stirred at 70° C. with 30 ml of tributyltin hydride. After 4 days, the solvent is distilled off and the residue chromatographed on silica gel with toluol/ethyl acetate. 3.5 g of 3-benzoyloxy-17α-(Z-2-tributylstannylvinyl) -1,3,5(10)-estratrien-17β-ol is isolated as oil.

760 mg of 3-benzoyloxy-17α-(Z-2-tributylstannylvinyl)-1,3,5(10)estratrien-17β-ol is stirred in 15 ml of tetrahydrofuran with 300 mg of N-iodosuccinimide at room temperature. After 45 min, it is diluted with ethyl acetate, washed with water, dried and concentrated in a vacuum. The crude product is stirred in 10 ml of methanol and 1.2 ml of water with 120 mg of sodium carbonate at room temperature. Addition of ethyl acetate, washing with water and drying are performed after 1 hour. The crude product is chromatographed on silica gel with hexane/ethyl acetate. 320 mg of 17α-(Z-2-iodovinyl)-1,3,5(10)-estratriene-3,17β-diol is obtained.

Melting point: 95° C. (decomposition).

(b) 10.0 g of 3,17β-diacetoxy-17α-ethinyl-1,3,5(10)-estratriene is stirred in 150 ml of N-methylpyrrolidone and 80 ml of tributyltin hydride at 70° C. After 48 hours it is diluted with ethyl acetate and washed several times with water, dried and concentrated in a vacuum to a large extent. After chromatographing of the crude product on silica gel with toluol/ethyl acetate 2.9 g of 17β-acetoxy-17α-(Z-2-tributylstannylvinyl)-1,3,5(10)-estratrien-3-ol is obtained as oil.

510 mg of 17β-acetoxy-17α-(Z-2-tributylstannylvinyl)-1,3,5(10)-estratrien-3-ol is stirred at room temperature with 250 mg of N-iodosuccinimide in 15 ml of tetrahydrofuran. After 30 minutes it is diluted with ethyl acetate, washed with water, dried and concentrated in a vacuum. The crude product is stirred in 8 ml of methanol and 1 ml of water with 100 mg of sodium carbonate at room temperature. After 1 hour it is diluted with ethyl acetate, washed with water, dried and concentrated in a vacuum. The crude product is chromatographed on silica gel with hexane/ethyl acetate. 240 mg of 17α-(Z-2-iodovinyl)-1,3,5(10)-estratriene-3,17β-diol is obtained.

Melting point: 97° C. (decomposition).

EXAMPLE 2

17α-(Z-2-bromovinyl)-1,3,5(10)-estratriene-3,17β-diol 630 mg of 3-benzoyloxy-17α-(Z-2-tributylstannylvinyl)-1,3,5(10)-estratrien-17β-ol is stirred in 12 ml of tetrahydrofuran with 280 mg of N-bromosuccinimide at room temperature. The reaction mixture is diluted after 30 min with ethyl acetate, washed with water, dried and concentrated in vacuum. The residue is dissolved in a mixture of 8 ml of methanol and 1 ml of water and stirred with 100 mg of sodium carbonate at room temperature. The reaction mixture is taken up in ethyl acetate, washed with water and dried. After chromatographing of the crude product with hexane/ethyl acetate, 270 mg of 17α-(Z-2-bromovinyl)-1,3,5(10)-estratrien-3,17β-diol is obtained.

Melting point: 93° C. (decomposition).

EXAMPLE 3

17α-(Z-2-iodovinyl)-3-methoxy-1,3,5(10)-estratriene-17β-ol 8.0 of 17α-ethynyl-3-methoxy-1,3,5(10)-estratrien-17β-ol is reacted with tributyltin hydride analogously to example 1. 2.1 g of 3-methoxy-17α(Z-2-tributylstannylvinyl)-1,3,5(10)-estratrien-17β-ol is obtained as oil.

900 mg of 3-methoxy-17α-(Z-2-tributylstannylvinyl)-1,3,5(10)-estratrien-17β-ol is reacted in 15 ml of tetrahydrofuran and 400 mg of N-iodosuccinimide at room temperature. After 45 min it is diluted with ethyl acetate, washed with water and dried. The crude product is chromatographed with hexane/ethyl acetate. 470 mg of 17α-(2-iodovinyl)-3-methoxy-1,3,5(10)-estratrien-17β-ol is isolated as foam.

EXAMPLE 4

17α-(Z-2-iodovinyl)-7α-methyl-1,3,5(10)-estratriene-3,17β-diol 3.9 g of 17α-ethynyl-7α-methyl-1,3,5(10)-estratriene-3,17β-diol (DE AS No. 1 443 683 (1969)) is reacted in 40 ml of N-methylpyrrolidone with 40 ml of tributyltin hydride at 70° C. The reaction mixture is diluted with ethyl acetate after 48 hours, washed several times with water, dried and concentrated to a large extent in a vacuum. After chromatographing of the crude product with toluol/ethyl acetate, 1.4 g of 7α-methyl-17α-(Z-2-tributylstannylvinyl)- 1,3,5 (10)-estratriene-3,17β-diol is obtained as oil.

620 mg of 7α-methyl-17α-(Z-2-tributylstannylvinyl)-1,3,5(10)-estratriene-3,17β-diol is reacted with N-iodosuccinimide analogously to example 3. 340 mg of 17 α-(Z-2-iodovinyl)-7α-methyl-1,3,5(10)-estratriene-3,17β-diol is obtained.

EXAMPLE 5

17α-(Z-2-bromovinyl)-7α-methyl-1,3,5(10)-estratriene-3,17β-diol 420 mg of 7α-methyl-17α-(Z-2-tributylstannylvinyl)-1,3,5(10)-estratriene- 3,17β-diol is reacted in 10 ml of tetrahydrofuran with 260 mg of N-bromosuccinimide at room temperature. After 30 min, it is diluted with ethyl acetate, washed with water and dried. After chromatographing on silica gel with hexane/ethyl acetate, 210 mg of 17α-(Z-2-bromovinyl)-7α-methyl-1,3,5(10)-estratriene-3,17β-diol is obtained as foam.

EXAMPLE 6

17α-(Z-2-iodovinyl)-1,3,5(10)-estratriene-1,3,17β-triol 5.6 g of 1,3-diacetoxy-17α-ethinyl-1,3,5(10)-estratrien-17β-ol (U.S. Pat. No. 3,418,415 (1968)) is reacted with tributyltin hydride analogously to example 4. 1.6 g of 17α-(Z-2-tributylstannylvinyl)-1,3,5(10)-estratriene-1,3,17β-triol is obtained as oil.

380 mg of 17α-(Z-2-tributylstannylvinyl)-1,3,5(10)-estratriene-1,3,17β-triol is reacted with N-iodosuccinimide analogously to example 3. 130 mg of 17α-(Z-2-iodovinyl)-1,3,5(10)-estratriene-1,3,17β-triol is obtained.

EXAMPLE 7

17α-(Z-2-bromovinyl)-1,3,5(10)-estratriene-1,3,17β-triol 510 mg of 17α-(Z-2-tributylstannylvinyl)-1,3,5(10)-estratriene-1,3,17β-triol is reacted with N-bromosuccinimide analogously to example 5. Yield 240 mg of 17α-(Z-2-bromovinyl)-1,3,5(10)-estratriene-1,3,17β-triol.

EXAMPLE 8

17α-(Z-2-iodovinyl)-18-methyl-1,3,5(10)-estratriene-3,17β-diol 4.0 g of 17α-ethynyl-18-methyl-1,3,5(10)-estratriene-3,17β-diol (U.S. Pat. No. 3,519,714 (1970)) is reacted with tributyltin hydride analogously to example 4. 1.8 g of 18-methyl-17α-(Z-2-tributylstannylvinyl)-1,3,5(10)-estratriene-3,17β-diol is isolated as oil.

800 mg of 18-methyl-17α-(Z-2-tributylstannylvinyl)-1,3,5(10)-estratriene-3,17β-diol is reacted with N-iodosuccinimide analogously to example 3. 380 mg of 17α-(Z-2-iodovinyl)-18-methyl-1,3,5(10)-estratriene-3,17β-diol is obtained.

EXAMPLE 9

17α-(Z-2-bromovinyl)-18-methyl-1,3,5(10)-estratriene-3,17β-diol 650 mg of 18 methyl-17α-(Z-2-tributylstannylvinyl)-1,3,5(10)-estratriene-3,17β-diol is reacted with N-bromosuccinimide analogously to example 5. 310 mg of 17α-(Z-2-bromvinyl)-18-methyl-1,3,5(10)-estratriene-3,17β-diol is obtained.

EXAMPLE 10

17α-(Z-2-iodovinyl)-8α-estra-1,3,5(10)-triene-3,17β-diol 5.0 g of 17α-ethynyl-8α-estra-1,3,5(10)-triene-3,17β-diol (U.S. Pat. No. 3,407,217 (1968)) is reacted with tributyltin hydride analogously to example 4. 2.2 g of 17α-(Z-2-tributylstannylvinyl)-8α-estra-1,3,5(10)-triene-3,17β-diol is obtained as oil.

2.1 g of 17α-(Z-2-tributylstannylvinyl)-8α-estra-1,3,5(10)-triene-3,17β-diol is reacted with N-iodosuccinimide analogously to example 3. 980 mg of 17α-(Z-2-iodovinyl)-8α-estra-1,3,5(10)-triene-3,17β-diol is obtained.

EXAMPLE 11

17α-(Z-2-bromovinyl)-8α-estra-1,3,5(10)-triene-3,17β-diol 1.3 g of 17α-(Z-2-tributylstannylvinyl)-8α-estra-1,3,5(10)-triene-3,17β-diol is reacted analogously to example 5. 610 mg of 17α-(Z-2-bromovinyl)-8α-estra-1,3,5(10)-triene-3, 17β-diol is obtained.

EXAMPLE 12

17α-(Z-2-iodovinyl)-11β-methoxy-1,3,5(10)-estratriene-3,17β-diol 4.0 g of 17α-ethinyl-11β-methoxy-1,3,5(10)-estratriene-3,17β-diol (U.S. Pat. No. 3,579,545 (1971)) is reacted with tributyltin hydride analogously to example 4. 1.8 g of 11β-methoxy-(Z-2-tributylstannylvinyl)-1,3,5(10)-estratriene-3,17β-diol is isolated as oil.

850 mg of 11β-methoxy-17α-(Z-2-tributylstannylvinyl)-1,3,5(10)-estratriene-3,17β-diol is reacted with N-iodosuccinimide analogously to example 3. 380 mg of 17α-(Z-2-iodovinyl)-11β-methoxy-1,3,5(10)-estratriene-3,17β-diol is obtained.

EXAMPLE 13

17α-(Z-2-bromovinyl)-11β-methoxy-1,3,5(10)-estratriene-3,17β-diol 350 mg of 11β-methoxy-17α-(Z-2-tributylstannylvinyl)-1,3,5(10)-estratriene-3,17β-diol is reacted analogously to example 5. 150 mg of 17α-(Z-2-bromovinyl)-11β-methoxy-1,3,5(10)-estratriene-3,17β-diol is obtained.

EXAMPLE 14

17α-(Z-2-iodovinyl)-11β-methyl-1,3,5(10)-estratriene-3,17β-diol 2.3 g of 17α-ethinyl-11β-methyl-1,3,5(10)-estratriene-3,17β-diol (DE AS No. 1 593 444 (1976)) is reacted with tributyltin hydride analogously to example 4. 900 mg of 11β-methyl-17α-(Z-2-tributylstannylvinyl)-1,3,5(10)-estratriene-3,17β-diol is obtained as oil.

350 mg of 11β-methyl-17α-(Z-2-tributylstannylvinyl)-1,3,5(10)-estratriene-3,17β-diol is reacted with N-iodosuccinimide analogously to example 3. 160 mg of 17α-(Z-2-iodovinyl)-11β-methyl-1,3,5(10)-estratriene-3,17β-diol is obtained.

EXAMPLE 15

17α-(Z-2-bromovinyl)-11β-methyl-1,3,5(10)-estratriene-3,17β-diol 300 mg of 11β-methyl-17α-(Z-2-tributylstannylvinyl)-1,3,5(10)-estratriene-3,17β-diol is reacted with N-bromosuccinimide analogously to example 5. 110 mg of 17α-(Z-2-bromovinyl)-11β-methyl-1,3,5(10)-estratriene-3,17β-diol is isolated.

EXAMPLE 16

17α-(E-2-bromovinyl)-1,3,5(10)-estratriene-3,17β-diol 10.0 g of 3-benzoyloxy-17α-ethinyl-1,3,5(10)-estratrien-17β-ol is stirred in 200 ml of tetrahydrofuran at 70° C. with 30 ml of tributyltin hydride and 2.0 g of α,α'-azoisobutyronitrile. After 30 min the reaction mixture is concentrated to a large extent in a vacuum. After chromatographing of the residue on silica gel with toluol/ethyl acetate, 16.3 g of 3-benzoyloxy-17α-(E-2-tributylstannylvinyl)-1,3,5(10)-estratrien-17β-ol is isolated as oil.

3.0 g of 3-benzoyloxy-17α-(E-2-tributylstannylvinyl)-1,3,5(10)-estratrien-17β-ol is reacted with N-bromosuccinimide analogously to example 2. After saponification of the 3-benzoate, 1.3 g of 17α(E-2-bromovinyl)-1,3,5(10)-estratriene-3,17β-diol is obtained.

EXAMPLE 17

17α-(E-2-bromovinyl)-3-methoxy-1,3,5(10)-estratrien-17β-ol 6.0 g of 17α-ethinyl-3-methoxy-1,3,5(10)-estratrien-17β-ol is reacted with tributyltin hydride analogously to example 16. 8.2 g of 3-methoxy-17α-(E-2-tributylstannylvinyl)-1,3,5(10)-estratrien-17β-ol is obtained as oil.

1.5 g of 3-methoxy-17α-(E-2-tributylstannylvinyl)-1,3,5(10)-estratrien-17β-ol is reacted with N-bromosuccinimide analogously to example 5. 710 mg of 17α-(E-2-bromovinyl)-3-methoxy-1,3,5(10)-estratrien-17β-ol is obtained.

EXAMPLE 18

17α-(E-2-iodovinyl)-7α-methyl-1,3,5(10)-estratriene-3,17β-diol 2.0 g of 17α-ethinyl-7α-methyl-1,3,5(10)-estratriene-3,17β-diol (DE AS No. 1 443 683 (1969)) is reacted with tributyltin hydride analogously to example 16. Yield 2.6 g of 7α-methyl-17α-(E-2-tributylstannylvinyl)-1,3,5(10)-estratriene-3,17β-diol as oil.

900 mg of 7α-methyl-17α-(E-2-tributylstannylvinyl)-1,3,5(10)-estratriene-3,17β-diol is reacted with N-iodosuccinimide analogously to example 3. Yield 540 mg of 17α-(E-2-iodovinyl)-7α-methyl-1,3,5(10)-estratriene-3,17β-diol.

EXAMPLE 19

17α-(E-2-bromovinyl)-7α-methyl-1,3,5(10)-estratriene-3,17β-diol 750 mg of 7α-methyl-17α-(E-2-tributylstannylvinyl)-1,3,5(10)-estratriene-3,17β-diol is reacted with N-bromosuccinimide analogously to example 5. Yield 370 mg of 17α-(E-2-bromovinyl)-7α-methyl-1,3,5(10)-estratriene-3,17β-diol.

EXAMPLE 20

17α-(E-2-iodovinyl)-1,3,5(10)-estratriene-1,3,17β-triol 2.3 g of 17α-ethinyl-1,3,5(10)-estratriene-1,3,17β-triol (U.S. Pat. No. 3,418,415 (1968)) is reacted with tributyltin hydride analogously to example 16. Yield 2.7 g of 17α-(E-2-tributylstannylvinyl)-1,3,5(10)-estratriene-1,3,17β-triol as oil.

1.2 g of 17α-(E-2-tributylstannylvinyl)-1,3,5(10)-estratriene-1,3,17β-triol is reacted with N-iodosuccinimide analogously to example 3. Yield 680 mg of 17α-(E-2-iodovinyl)-1,3,5(10)-estratriene-1,3,17β-triol.

EXAMPLE 21

17α-(E-2-bromovinyl)-1,3,5(10)-estratriene-1,3,17β-triol 450 mg of 17α-(E-2-tributylstannylvinyl)-1,3,5(10)-estratriene-1,3,17β-triol is reacted with N-bromosuccinimide analogously to example 5. Yield 180 mg of 17α-(E-2-bromovinyl)-1,3,5(10)-estratriene-1,3,17β-triol.

EXAMPLE 22

17α-(E-2-iodovinyl)-18-methyl-1,3,5(10)-estratriene-3,17β-diol 2.6 g of 17α-ethinyl-18-methyl-1,3,5(10)-estratriene-3,17β-diol (U.S. Pat. No. 3,519,714 (1970)) is reacted with tributyltin hydride analogously to example 16. Yield 2.9 g of 18-methyl-17α-(E-2-tributylstannylvinyl)-1,3,5(10)-estratriene-3,17β-diol as oil.

1.6 g of 18-methyl-17α-(E-2-tributylstannylvinyl)-1,3,5(10)-estratriene-3,17β-diol is reacted with N-iodosuccinimide analogously to example 3. Yield 840 mg of 17α-(E-2-iodovinyl)-18-methyl-1,3,5(10)-estratriene-3,17β-diol.

EXAMPLE 23

17α-(E-2-bromovinyl)-18-methyl-1,3,5(10)-estratriene-3,17β-diol 500 mg of 18-methyl-17α-(E-2-tributylstannylvinyl)-1,3,5(10)-estratriene-3,17β-diol is reacted with N-bromosuccinimide analogously to example 5. Yield 280 mg of 17α-(E-2-bromovinyl)-18-methyl-1,3,5(10)-estratriene-3,17β-diol.

EXAMPLE 24

17α-(E-2-iodovinyl)-8α-estra-1,3,5(10)-triene-3,17β-diol 2.5 g of 17α-ethinyl-8α-estra-1,3,5(10)-triene-3,17β-diol (U.S. Pat. No. 3,407,217 (1968) is reacted with tributyltin hydride analogously to example 16. Yield 2.7 g of 17α-(E-2-tributylstannylvinyl)-8α-estra 1,3,5(10)-triene-3,17β-diol as oil.

1.2 g of 17α-(E-2-tributylstannylvinyl)-8α-estra-1,3,5(10)-triene-3,17β-diol is reacted with N-iodosuccinimide analogously to example 3. Yield 700 mg of 17α-(E-2-iodovinyl)-8α-estra-1,3,5(10)-triene-3,17β-diol.

EXAMPLE 25

17α-(E-2-bromovinyl)-8α-estra,1,3,5(10)-triene-3,17β-diol 900 mg of 17α-(E-2-tributylstannylvinyl)-8α-estra-1,3,5(10)-triene-3,17β-diol is reacted with N-bromosuccinimide analogously to example 5. Yield 360 mg of 17α-(E-2-bromovinyl)-8α-estra-1,3,5(10)-triene-3,17β-diol.

EXAMPLE 26

17α-(E-2-bromovinyl)-11β-methoxy-1,3,5(10)-estratriene-3,17β-diol 2.3 g of 17α-ethinyl-11β-methoxy-1,3,5(10)-estratriene-3,17β-diol (U.S. Pat. No. 3,579,545 (1971)) is reacted with tributyltin hydride analogously to example 16. Yield 2.4 g of 11β-methoxy-17α-(E-2-tributylstannylvinyl)-1,3,5(10)-estratriene-3, 17β-diol as oil.

550 mg of 11β-methoxy-17α-(E-2-tributylstannylvinyl)-1,3,5(10)-estratriene-3,17β-diol is reacted with N-bromosuccinimide analogously to example 5. Yield 230 mg of 17α-(E-2-bromovinyl)-11β-methoxy-1,3,5(10)-estratriene-3,17β-diol.

EXAMPLE 27

17α-(E-2-iodovinyl)-11β-methyl-1,3,5(10)-estratriene-3,17β-diol 2.0 g of 17α-ethinyl-11β-methyl-1,3,5(10)-estratriene-3,17β-diol (DE AS No. 1 593 444 (1976)) is reacted with tributyltin hydride analogously to example 16. Yield 2.2 g of 11β-methyl-17α-(E-2-tributylstannylvinyl)-1,3,5(10)-estratriene-3,17β-diol as oil.

1.1 g of 11β-methyl-17α-(E-2-tributylstannylvinyl)-1,3,5(10)-estratriene-3,17β-diol is reacted with N-iodosuccinimide analogously to example 3. Yield 600 mg of 17α-(E-2-iodovinyl)-11β-methyl-1,3,5(10)-estratriene-3,17β-diol.

EXAMPLE 28

17α-(E-2-bromovinyl)-11β-methyl-1,3,5(10)-estratriene-3,17β-diol 300 mg of 11β-methyl-17α-(E-2-tributylstannylvinyl)-1,3,5(10)-estratriene-3,17β-diol is reacted with N-bromosuccinimide analogously to example 5. Yield 120 mg of 17α-(E-2-bromovinyl)-11β-methyl-1,3,5(10)-estratriene-3,17β-diol.

EXAMPLE 29

50 μl of Na-$^{125}$I, containing 185 MBq$^{125}$I, as aqueous neutral solution is added to 500 μg of 17α-(Z-2-tributylstannylvinyl)-1,3,5(10)-estratriene-3,17β-diol in 250 μl of methyl ethyl ketone at room temperature. It is allowed to stand at room temperature for 5 min, the resulting materials are separated on an analytical HPTLC plate and the radioactive zone is eluted. The eluate is separated with a half preparative HPLC column with radioactivity monitor. There is obtained >148 MBq of pure 17α-(Z-2-$^{125}$-iodovinyl)-1,3,5(10)-estratriene-3,17β-diol in methanolic aqueous solution. The radioactive labeling is carrier-free. The specific activity corresponds to the radioactive iodine used.

Analogously as described for $^{125}$iodine, the compound is also obtained labeled with $^{123}$iodine, $^{131}$iodine and $^{132}$iodine, and also with $^{77}$bromine, $^{80m}$bromine and $^{82}$bromine.

EXAMPLE 30

5 μg (0.013 μmol) of 17α-(Z-2-bromovinyl)-17α-hydroxy-1,3,5(10)-estratriene-3,17β-diol diol is dissolved in 0.25 ml of diethylene glycol diethyl ether (dry) and heated 3 hours to 120° C. under protective gas in the presence of 370 MBq of sodium-($^{125}$I)iodide (carrier-free) and 1 μg of copper sulfate.

After cooling to ice-bath temperature, 0.25 ml of methanol, 0.1 ml of water and 1 μg of sodium iodide are added. The solution is passed through a mixed bed ion exchanger to remove the ions. 2 μg of 17α(Z-2[$^{125}$I]iodovinyl)-1,3,5(10)-estratriene-3,17β-diol with a specific activity, which corresponds to the sodium-($^{125}$I)iodide used, is obtained. Thus, it is in the order of magnitude of 80.29 GBq/μmol. The resulting 17α-(Z-2-iodovinyl)-1,3,5(10)-estratriene-3,17β-diol carrier-free labeled with $^{125}$I is separated from the initial product by chromatography on silica gel in a low-pressure column in the hexane/acetone system (acetone 10→30%). After concentration, taking up in ethanol/propylene glycol, a product suitable for diagnostic purposes is obtained.

EXAMPLE 31

1 mg of 17α-(Z-2-tributylstannylvinyl)-1,3,5(10)-estratriene-3,17β-diol (1 mg) in 2 ml of chloroform is added to a solution of $^{125}I_2$ [37 MBq] in 2 ml of carbon tetrachloride at room temperature. After 5 min, an aqueous solution of sodium bisulfate and potassium fluoride is added. The phases are shaken out and separated. The aqueous phase is washed twice with chloroform, the organic phases are combined, dried with magnesium sulfate, filtered and concentrated. Separation is performed on HPTLC plates, the radioactive strips are eluted with ethanol, and ≈37 MBq [$^{125}I$] of carrier-free labeled 17α(Z-2-idovinyl)-1,3,5(10)-estratriene-3,17β-diol is obtained.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 17α-bromo- or 17α-iodo-vinylestrane of the formula

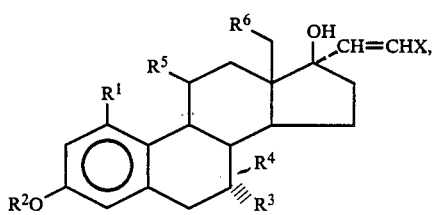

wherein
X is bromine or iodine, in Z or E position,
$R^1$ is hydroxy or alkanoyloxy of up to 3 C atoms,
$R^2$ is hydrogen, alkyl of up to 3 C atoms, alkanoyl of up to 7 C. atoms or benzoyl,
$R^3$ is hydrogen or methyl,
$R^4$ is hydrogen in the α or β position,
$R^5$ is hydrogen, methyl or methoxy, and
$R^6$ is hydrogen or methyl.

2. A compound of claim 1, wherein X is non-radioactive Br or I.
3. A compound of claim 1, wherein X is radioactive Br or I.
4. A pharmaceutical composition of claim 3, wherein X is radioactive and the carrier is adapted for diagnostic applications.
5. 17α-(Z-2-iodovinyl)-1,3,5(10)-estratriene-1,3,17β-triol, a compound of claim 1.
6. 17α-(Z-2-bromovinyl)-1,3,5(10)-estratriene-1,3,17β-triol, a compound of claim 1.
7. 17α-(E-2-iodovinyl)-1,3,5(10)-estratriene-1,3,17β-triol, a compound of claim 1.
8. 17α-(E-2-bromovinyl)-1,3,5(10)-estratriene-1,3,17β-triol, a compound of claim 1.
9. A pharmaceutical composition comprising an estrogenically effective amount of a compound of claim 1 and a pharmaceutically acceptable carrier.
10. A method for achieving an estrogenic effect in a patient comprising administering to the patient an estrogenically effective amount of a compound of claim 1.
11. A compound of claim 1 wherein $R^5$ is methoxy.
12. A compound of claim 1 wherein $R^2$ is alkanoyl or benzoyl.
13. In a method of performing a diagnosis comprising administering an estrogenic radioactive compound and then detecting the locus of the resultant radioactivity, the improvement wherein the compound is a compound of claim 1 wherein X is radioactive.
14. A 17α-bromo- or 17α-iodo-vinylestrane of the formula

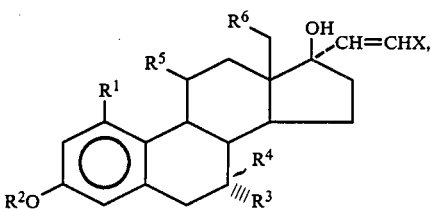

wherein
X is bromine or iodine, in Z or E position,
$R^1$ is hydrogen, hydroxy or alkanoyloxy of up to 3 C atoms,
$R_2$ is alkanoyl of up to 7 C atoms or benzoyl,
$R^3$ is hydrogen or methyl,
$R^4$ is hydrogen in the α or β position,
$R^5$ is hydrogen, methyl or methoxy, and
$R^6$ is hydrogen or methyl.

* * * * *